(12) United States Patent
Couillard et al.

(10) Patent No.: US 6,183,576 B1
(45) Date of Patent: Feb. 6, 2001

(54) MULTIPLE PATH BONDING

(75) Inventors: Jack L. Couillard, Menasha; Robin K. Nason, Oshkosh, both of WI (US)

(73) Assignee: Kimberly-Clark Worldwide, Inc., Neenah, WI (US)

(*) Notice: Under 35 U.S.C. 154(b), the term of this patent shall be extended for 0 days.

(21) Appl. No.: 09/321,366

(22) Filed: May 27, 1999

(51) Int. Cl.[7] ................................................. B32B 31/16
(52) U.S. Cl. ........................ 156/73.1; 156/227; 156/308.4
(58) Field of Search .................... 156/73.1, 227, 156/290, 308.2, 308.4, 580.1, 580.2; 264/442, 443, 444

(56) References Cited

U.S. PATENT DOCUMENTS

| | | | |
|---|---|---|---|
| 4,940,464 | 7/1990 | Van Gompel et al. | 604/396 |
| 5,096,532 | 3/1992 | Neuwirth et al. | 156/580.1 |
| 5,110,403 | 5/1992 | Ehlert | 156/580.1 |
| 5,440,764 | 8/1995 | Matsushita | 2/401 |
| 5,711,832 | * 1/1998 | Glaug et al. | 156/73.1 |
| 5,817,199 | * 10/1998 | Brennecke et al. | 156/73.1 |
| 5,961,758 | * 10/1999 | Honegger | 156/73.1 |

FOREIGN PATENT DOCUMENTS

97/47265    12/1997   (WO).

\* cited by examiner

*Primary Examiner*—James Sells
(74) *Attorney, Agent, or Firm*—Pauley Petersen Kinne & Fejer

(57) ABSTRACT

High speed, continuous processing of product pieces with desirably extended durations of application of bonding or bonding energy.

24 Claims, 4 Drawing Sheets

MULTIPLE PATH BONDING

FIELD OF THE INVENTION

This invention relates generally to processing involving the bonding together of two or more items or sections of a single item and, more particularly, to bond processing using multiple paths.

BACKGROUND OF THE INVENTION

Disposable absorbent pant-like garments for use as a child's training pants, adult incontinence garment and the like have grown in popularity and use. For example, Van Gompel et al., U.S. Pat. No. 4,940,464, issued Jul. 10, 1990, the disclosure of which is incorporated herein by reference in its entirety, discloses such garments and the manufacture thereof.

FIG. 1 is a perspective view of one embodiment of such a garment or pant, generally designated by the reference numeral 10, as it would appear on a wearer indicated in dash lines. The garment 10 generally comprises a waste containment section 12 and two side panels 14 and 16, respectively, defining a waist opening 20 and a pair of leg openings 22 and 24, respectively. More particularly, the side panel 14 is composed of a pair of stretchable side members 26 and 30 bonded together along or to form a seam 32. Similarly, the side panel 16 is composed of a pair of stretchable side members 36 and 40 bonded together along or to form a seam 42.

Various bonding techniques are available to effect bonding of such members or other member materials to form such side seams or the like. For example, one bonding technique which has found growing application involves the application of ultrasonic energy. For example, Neuwirth et al., U.S. Pat. 5,096,532, issued Mar. 17, 1992 and Ehlert, U.S. Pat. No. 5,110,403, issued May 5, 1992, the disclosures of each of which is incorporated herein by reference in its entirety, generally relate to ultrasonic rotary horns useful in such processing.

While various techniques are available for the bonding together of side members or the like, typically such bonding techniques involve or require prolonged bonding or dwell times in order to better ensure the formation and maintenance of proper and effective bonding of the side members. For example, bond strength is generally a function of dwell time, with correspondingly increased dwell times generally resulting in improved or stronger bond formation. As will be appreciated, such prolonged bond processing times can dramatically limit the rate at which such garments can be processed through a conventional process machinery line.

Thus, there is a need and a demand for processing improvements effective to avoid or minimize the rate limiting effects of bonding on the manufacturing line processing of such associated products.

SUMMARY OF THE INVENTION

A general object of the invention is to provide an improved process for the bonding of a series of pieces each to itself.

A more specific objective of the invention is to overcome one or more of the problems described above.

The general object of the invention can be attained, at least in part, through a high speed process for bonding a series of pieces each to itself. In accordance with one embodiment of the invention, such a process involves splitting a supplied series of pieces to be bonded into first and second subseries of pieces to be bonded. The first subseries of pieces to be bonded are subsequently bonded to form a first series of bonded pieces. Similarly, the second subseries of pieces to be bonded are bonded to form a second series of bonded pieces.

The prior art generally fails to provide methods or processing techniques which provide desirably prolonged or extended dwell times, such as may be desired for at least certain types of bonding, in the context of high speed manufacture or processing. More particularly, the prior art generally fails to provide such desirably prolonged or extended dwell times relative to such bond formation via the application of ultrasonic or thermal energy or the like.

The invention further comprehends a continuous high speed process for ultrasonic bonding a series of pieces each to itself. In accordance with one embodiment of the invention, such a process involves alternatingly splitting a series of pieces to be bonded into first and second subseries of pieces to be bonded. Members of the first subseries of pieces to be bonded are folded into bonding relative position. Members of the second subseries of pieces to be bonded are folded into bonding relative position. The folded first subseries of pieces to be bonded are ultrasonically bonded to form a first series of bonded pieces. The folded second subseries of pieces to be bonded are ultrasonically bonded to form a second series of bonded pieces.

In accordance with another preferred embodiment of the invention, there is provided a process for side seam bonding of a disposable pant-like garment for absorbing human discharge. The process involves supplying a series of planar garment precursor pieces to be bonded. The series of pieces to be bonded is alternatingly split into first and second subseries of pieces to be bonded. The members of the first and second subseries of pieces to be bonded are folded into bonding relative position. The folded members of the first subseries of pieces to be bonded are sequentially ultrasonically bonded to form a first series of bonded pieces and the folded members of the second subseries of pieces to be bonded are sequentially ultrasonically bonded to form a second series of bonded pieces in a manner wherein a folded member of the first subseries of pieces to be bonded and a folded member of the second subseries of pieces to be bonded are bonded substantially simultaneously.

Other objects and advantages will be apparent to those skilled in the art from the following detailed description taken in conjunction with the appended claims and drawings.

DETAILED DESCRIPTION OF THE PRESENTLY PREFERRED EMBODIMENTS

The present invention, as is described in more detail below, provides an improved process for bonding a series of pieces each to itself.

While the invention is described below with particular reference to side seam bonding, such as by application of ultrasonic energy, of a disposable pant-like garment for absorbing human discharge, it is to be understood that the invention also has applicability to not only other bonding techniques such as thermal bonding, for example, but also can, if desired, be used to process other types or kinds of pieces being bonded.

Figure 2:
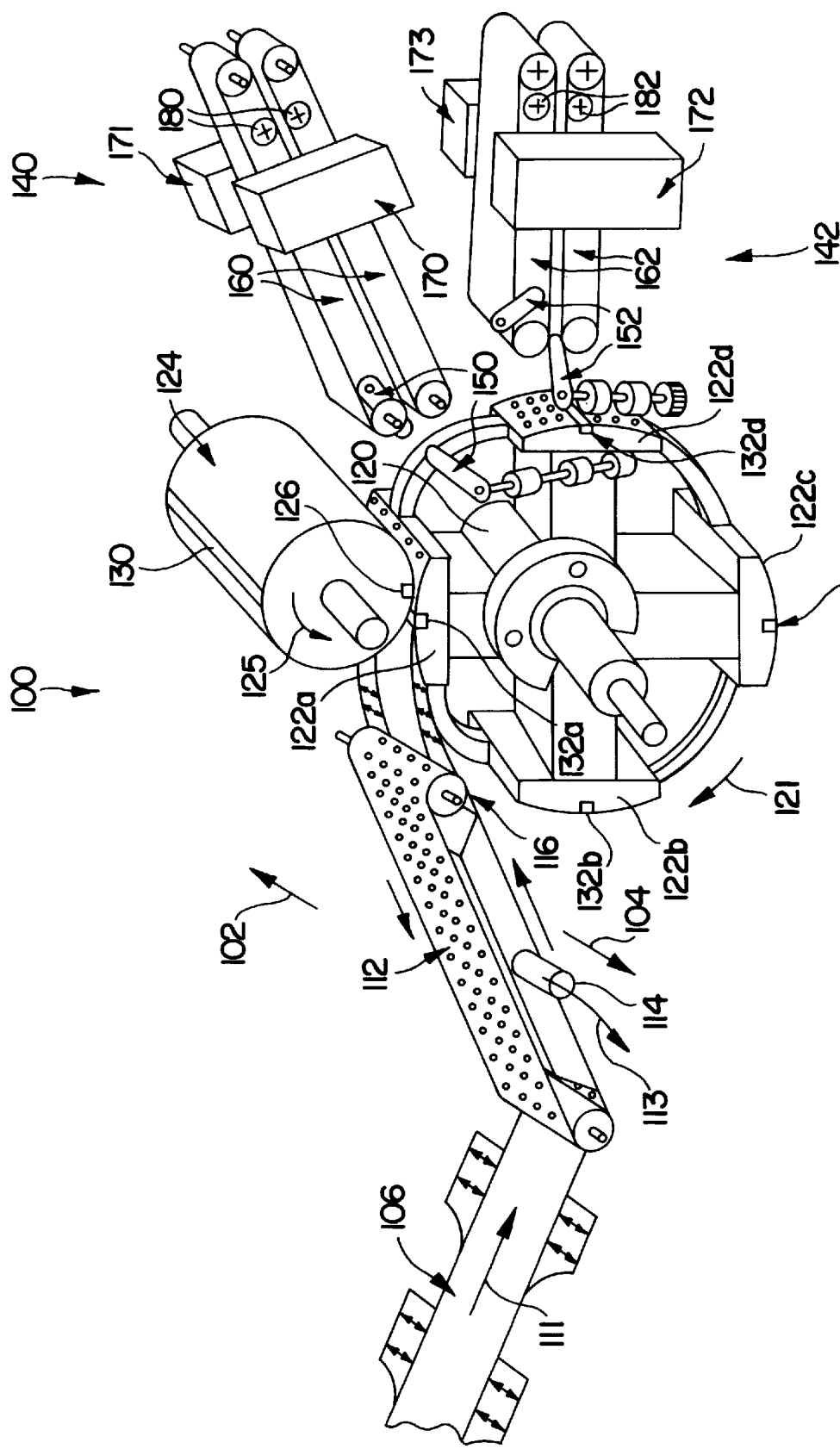
FIG. 2 is a simplified perspective schematic of a processing assembly in accordance with one embodiment of the invention.

Referring to the drawings and initially referring particularly to FIG. 2, there is illustrated a simplified schematic of a processing assembly, generally designated by the reference numeral 100, in accordance with one embodiment of the invention. To facilitate discussion and description, the opposed sides of the processing assembly 100 are herein generally referred to as the drive side and the operator side, as signified by the arrows 102 and 104, respectively.

As shown, a continuous web 106 is introduced to the processing assembly 100 such as via a conveyor belt and has a direction of travel signified by the arrow 111. In accordance with one preferred embodiment of the invention, the continuous web 106, also commonly referred to as a "sausage," is generally composed of various layers of materials such as desired and included in the particular product being processed. For example, for a disposable pant-like garment for absorbing human discharge herein described, such a continuous web or sausage 106 is generally an assembly composed of one or more layers of material. While such disposable pant-like garment for absorbing human discharge can be variously constructed, in practice the pant-like garment will include one or more liquid-pervious liners, absorbent inserts, and a liquid impervious outer cover such as composed of a cloth-like material. The continuous web 106 additionally may generally include flaps, waist band elastic, leg elastics, etc. or the like such as may serve to facilitate the placement and attachment of the final product onto an appropriate individual. In practice, the continuous web will have a repeat length which will be dependent on the grade or size of the specific garment product being manufactured. For example, a children's training pant garment will typically be formed using a continuous web having a repeat length of about 16 to about 32 inches with the specific repeat length again being dependent on the grade or size of the training paint garment being formed.

It will be understood, however, that the broader practice of the invention is not limited by the specific construction, shape, form or size of the web or the product being processed. For example, if desired, the invention can be practiced in conjunction with a web composed of a single material.

In the processing assembly 100, the continuous web 106 is transferred to a vacuum incline conveyor 112. With such a conveyor, a vacuum is created or generated, such as is known in the art and such as may serve to hold the web 106 to the underside thereof and to pull the web at full web speed. For example, such a vacuum can be created by a fan (not shown) pulling air (signified by the arrow 113) out through the duct 114 on the operator side 104. Alternatively or in addition, such a vacuum could be created by drawing air from the drive side 102, if desired.

The vacuum of the conveyor 112 is turned off or released at or about the tangent point 116. The web 106 is there transferred onto a vacuum folding drum 120 whereat a vacuum is created or generated, such as is known in the art and such as may serve to hold the web 106 thereto. The vacuum folding drum 120 has a direction of rotation signified by the arrow 121. In the illustrated embodiment, the folding drum 120 includes four (4) plates or stations 122(*a–d*). For example, each such plate or station 122(*a–d*) may be of a vacuum form timed to form or "pull" a vacuum at the transfer tangent point 116 with the vacuum incline conveyor 112 and such as to effect the transfer of the web 106 thereon. It is to be understood, however, that the broader practice of the invention is not limited by the number of plates or stations of the folding drum and folding drums. For example, folding drums with greater or fewer number of plates or stations can, if desired, be used.

In the processing assembly 100, the web 106 on the plate 122*a* is acted upon by a knife roll 124 which has a direction of rotation signified by the 125. The knife roll 124 includes first and second cuffing edges 126 and 130, respectively. More specifically, the knife roll cutting edge 126 contacts a blade cutting surface 132*a* on the plate 122*a* or otherwise serves to cut the web 106 into discrete, generally planar pieces prior to the folding of such pieces. As shown, each of the plates 122(*a–d*) may incorporate or include a corresponding blade cutting surface 132(*a–d*). As will be appreciated, the broader practice of the invention is not limited by the number of cutting edges as for example, knife rolls with one or more cutting edges can be used. Further, suitable cutting devices other than knife rolls and such as known in the art can, if desired, be used.

The processing assembly 100 then forms or consists of a first or upper process line 140 and a second or lower process line 142 such as to respectively process first and second subseries of pieces to be bonded. The process lines 140 and 142 are generally similar to each other and are designed to facilitate the high speed processing of product pieces while providing relatively extended bond dwell times for the product pieces being processed therethrough.

The processing assembly 100 includes first and second station pairs of folding blade assemblies 150 and 152, respectively, whereby members of the first and second subseries of pieces to be bonded are folded into bonding relative position. The construction and operation of such folding blades are well known in the art and do not form limitations on the broader practice of the present invention. In general, each of the pairs of folding blades 150 and 152, respectively, are timed and synchronized to make one revolution every two product pieces such that in a series of product pieces, every other product piece is folded by the first station pair of folding blades 150 while each of the alternating product pieces is folded by the second pair of folding blades 152. As a result of such processing, a series of pieces to be bonded is alternatingly divided into first and second subseries of pieces to be bonded.

Figure 1:
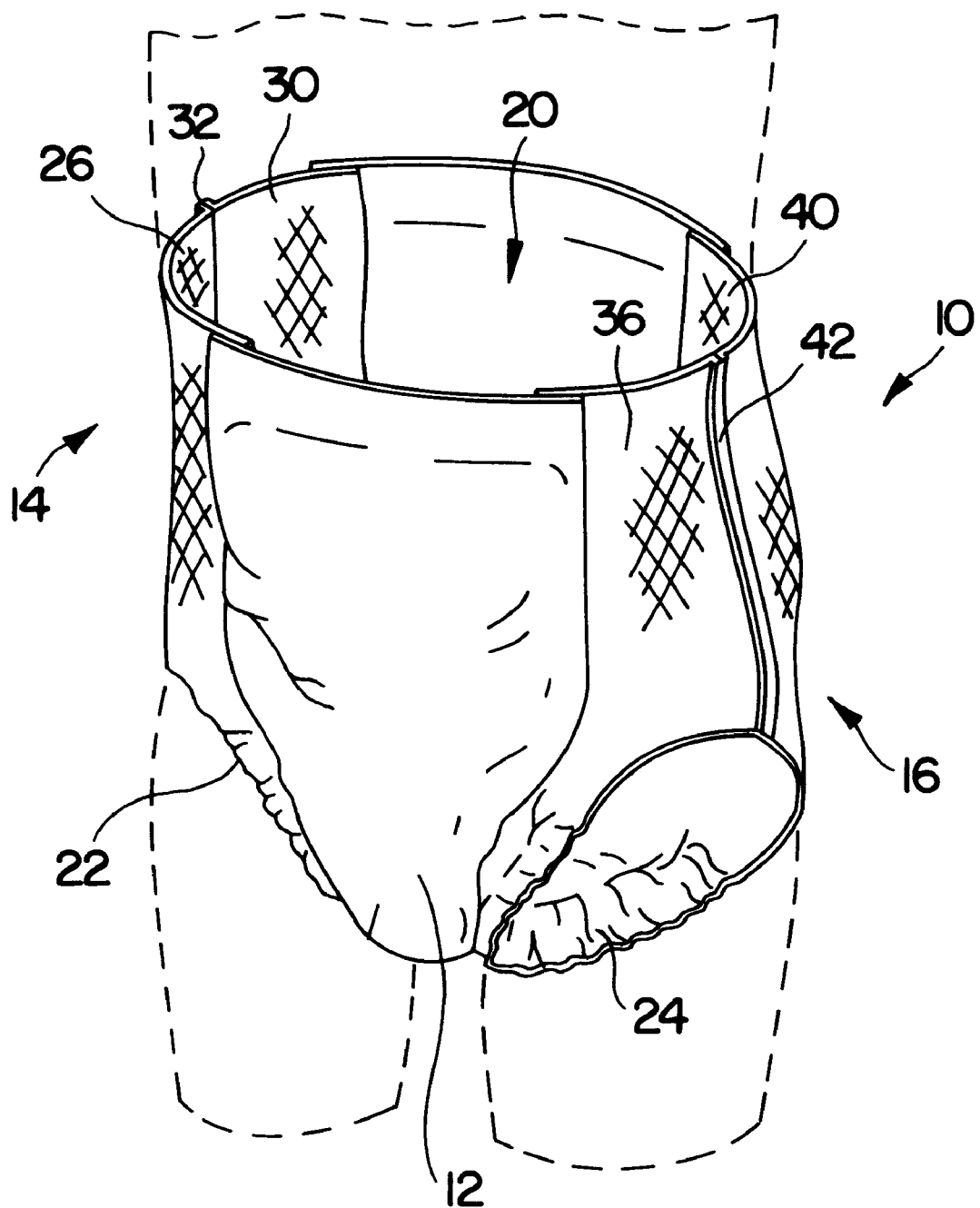
FIG. 1 is a simplified perspective view of one embodiment of a disposable absorbent pant-like garment as it would appear on a wearer indicated in dash lines.

Associated with the first and second station pairs of folding blades 150 and 152 are first and second variable speed conveyor assemblies 160 and 162, respectively, such as in the form of smooth belt conveyors that can act to nip and convey the folded product pieces for subsequent processing in accordance with the invention. Associated with each of the first and second conveyor assemblies 160 and 162 is a pair of bonders 170 and 171, respectively, for the process line 140 and bonders 172 and 173, respectively, for the process line 142. The bonders are effective to form a bond, specifically a side seam bond such as the side seam bonds 32 and 42, respectively, shown in the garment 10 in FIG. 1, with each of such pairs of bonders forming a side seam bond on the opposed sides of a folded product piece processed therethrough. In a preferred embodiment of the invention such oppositely disposed side seams are formed substantially simultaneously.

Various bonding techniques are available to effect bonding of such members or other member materials such as to form such side seams or the like. For example, as identified above, such bonding techniques may involve the application of ultrasonic energy. Alternatively, such bonding may take the form of thermal bonding such as involving the application of thermal energy to the piece or pieces being bonded. As will be appreciated by those skilled in the art, other bonding techniques such as known in the art may, if desired, be used.

In accordance with the invention, the conveyors 160 and 162 do not run at a constant speed. Rather, the conveyors 160 and 162 run at an operating speed which is about 10% faster than the tip velocities of the associated folding blades 150 and 152, respectively, during the time period the folding blades are interacting with the conveyors. The conveyors 160 and 162 then run at a reduced speed in conveying product pieces through the seam bonder pairs 170 and 171, respectively, and 172 and 173, respectively. As will be appreciated, such reduced conveyance speed through the bonders is often helpful in providing an extended bond dwell time such as may be desired or required to effect bonding of desired strength.

Various means and techniques, such as known in the art, are available whereby the conveyance speed of the conveyors 160 and 162 can be variably controlled. For example, such take away conveyors can desirably be controlled such as by elliptical gearing or servo motors such that the conveyors travel at full web speed during folding but slow down to a speed of about one-fourth of full web speed as the respective pieces to be bonded are passed through the corresponding bonder.

In practice, it will be appreciated that through such processing arrangement, each of the process lines 140 and 142, respectively, need process (e.g., bond) a respective subseries of pieces to be bonded at a speed of no more than about one-half and, desirably, at about one-fourth the speed at which pieces to be bonded are discharged or produced with the folding drum 120. As will be appreciated, such bond processing speeds can be further correspondingly reduced such as through the inclusion of additional similar such processing lines.

While the use of variable speed conveyor assemblies such as the above-described conveyor assemblies 160 and 162 are one preferred arrangement for providing the desired extended processing times through associated bonders, it will be understood that the broader practice of the invention is not necessarily so limited. For example, if desired, the invention can alternatively be practiced with a process line composed of a combination of a first constant speed conveyor to initially accept folded product pieces from the respective station folding blades, followed by a processing conveyor to process the folded product pieces through an associated bonder. In practice, such first constant speed conveyors will preferably run or operate at a conveyance speed of about 0 to 10% faster than the speed at which pieces to be bonded are discharged or produced with the associated folding drum such as to avoid undesired processing backups. The following processing conveyors can, in turn, desirably operate at a conveyance speed of no more than about one-half and, desirably, at about one-fourth the speed at which pieces to be bonded are discharged or produced with the associated folding drum in order to provide desired extended processing times through an associated bonder.

Each of the process lines 140 and 142 may additionally include post-bonding processing apparatuses such as shear slitters 180 and 182 such as may be desired to assist in the removal of excess material from the bonded product pieces.

The bonded pieces can then be subjected to various particular processing operations, such as known in the art. For example, such bonded pieces can be subsequently processed such as through tucking, stacking and packaging sections, such as known in the art.

Figure 3:
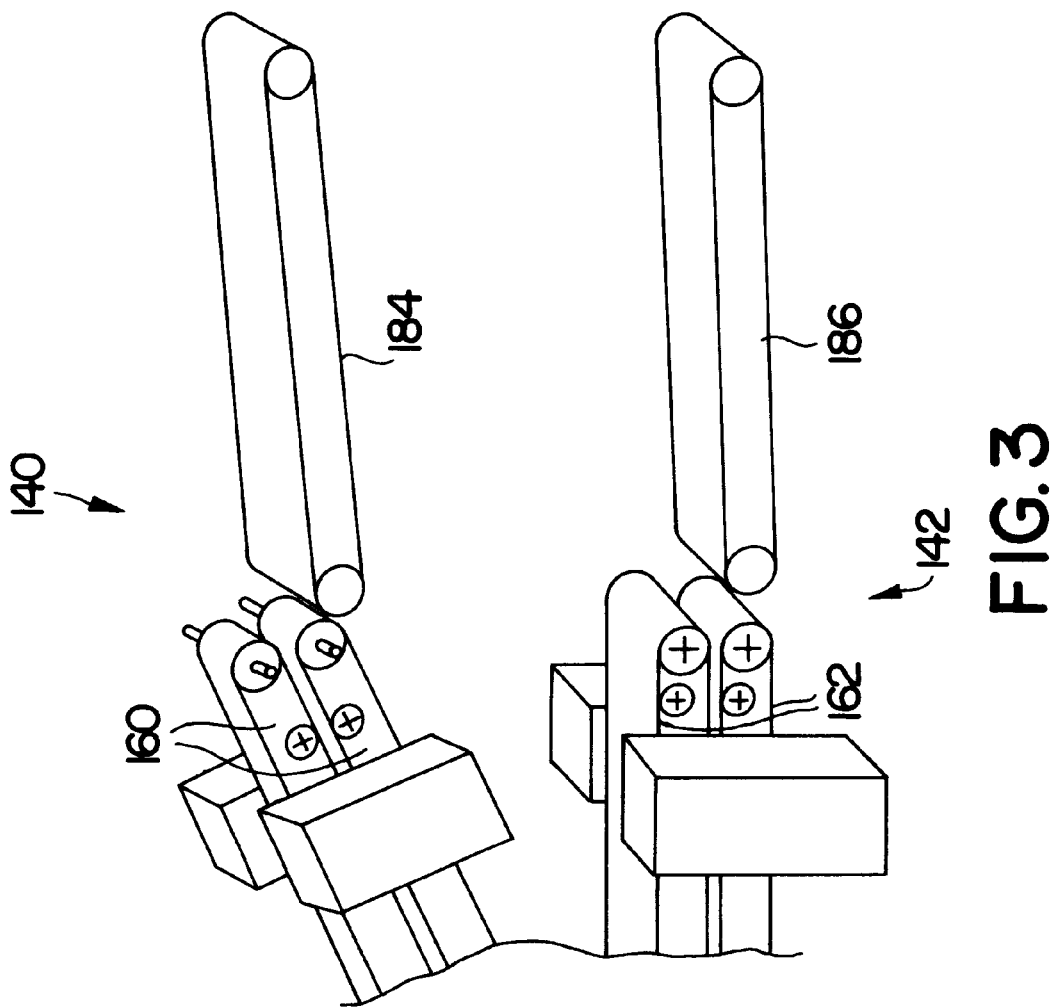
FIG. 3 is a simplified fragmentary side view schematic illustrating piece processing following bonding in accordance with one embodiment of the invention.

In accordance with certain preferred embodiments of the invention and as shown in FIG. 3, the resulting bonded product pieces of the first and second processing lines 140 and 142, respectively, such as supplied by the conveyors 160 and 162, respectively, can be further processed separately such as via the conveyors 184 and 186, respectively.

Figure 4:
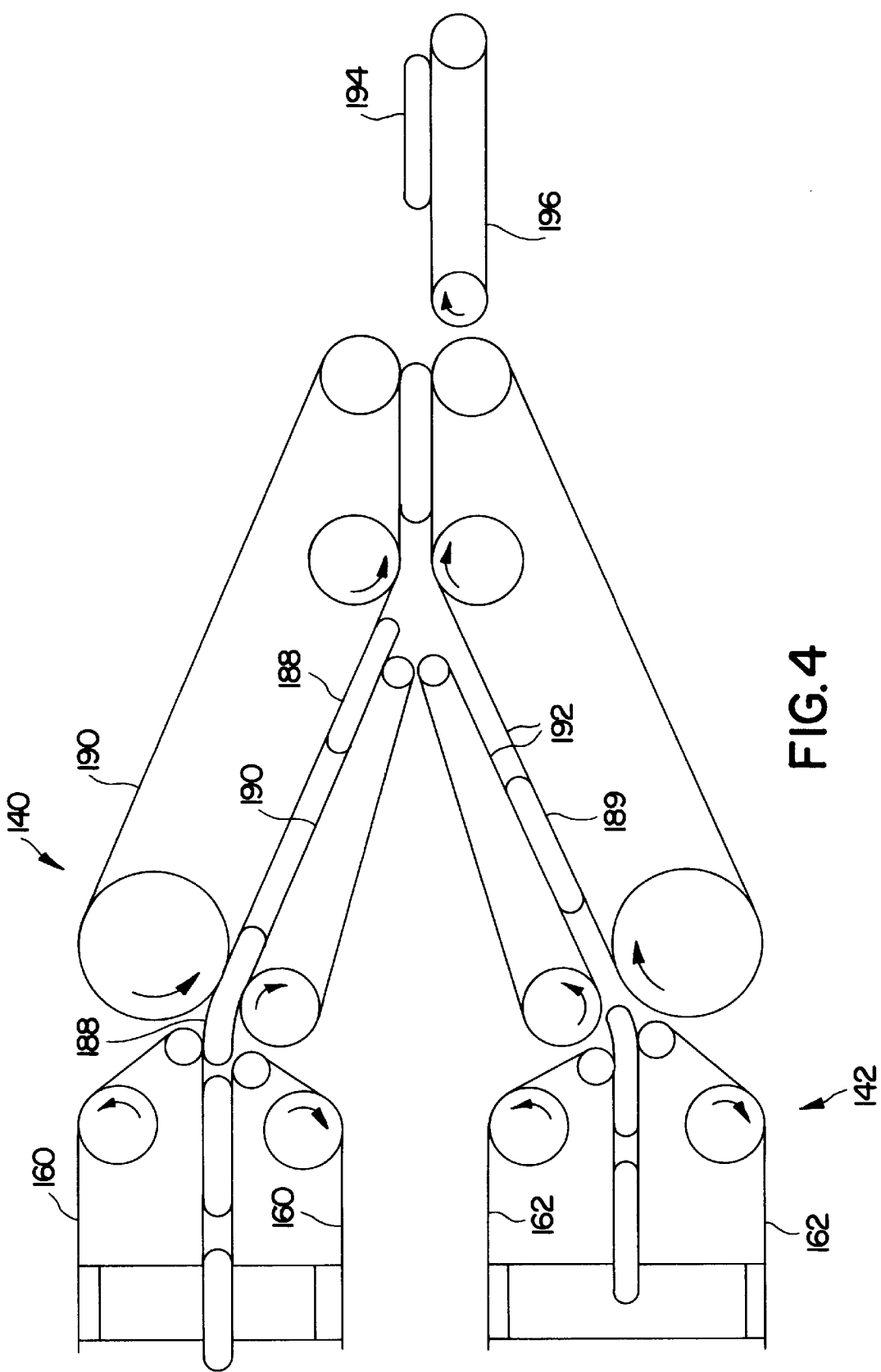
FIG. 4 is a simplified fragmentary side view schematic illustrating piece processing following bonding in accordance with an alternative embodiment of the invention.

Alternatively, in accordance with one preferred embodiment of the invention and as shown in FIG. 4, the resulting bonded product pieces of the first processing line 140 such as supplied by the conveyors 160 (such product pieces here designated with the reference numeral 188) and the resulting bonded product pieces of the second processing line 142 such as supplied by the conveyors 162 (such product pieces here designated with the reference numeral 189) can be recombined such as by means of recombining conveyors 190 and 192 to form a single product stream 194. The product stream 194 can then be conveyed by a product conveyor 196. Such combining of the resulting product pieces of the separate processing lines 140 and 142 for subsequent processing (e.g., tucking, stacking, packaging, etc.) can dramatically reduce equipment costs and operating efficiencies by processing the bonded product pieces through the same processing equipment.

In view of the above, it will be appreciated that methods or processing techniques of the present invention generally provide or result in desirably prolonged or extended dwell times, such as may be desired for at least certain types of bonding, in the context of high speed manufacture or processing. More particularly, the invention generally provides such desirably prolonged or extended dwell times relative to such bond formation via the application of ultrasonic or thermal energy or the like.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

We claim:

1. A high speed process for bonding a series of pieces each to itself comprising:

supplying a series of pieces to be bonded, splitting the series of pieces to be bonded into first and second subseries of pieces to be bonded, bonding the first subseries of pieces to be bonded to form a first series of bonded pieces, and bonding the second subseries of pieces to be bonded to form a second series of bonded pieces.

2. The process of claim 1 wherein said splitting comprises providing alternating pieces to be bonded from the series of pieces to be bonded to form the first and second subseries of pieces to be bonded, respectively.

3. The process of claim 1 additionally comprising, combining the first and second series of bonded pieces to form a unified series of bonded product.

4. The process of claim 1 wherein the series of pieces to be bonded are supplied at a first speed and the first and second subseries of pieces to be bonded are bonded at a speed of no more than about half the first speed.

5. The process of claim 1 additionally comprising,
separately further processing each of the first and second series of bonded pieces, respectively.

6. The process of claim 1 wherein said splitting includes folding members of the first and second subseries of pieces to be bonded.

7. The process of claim 1 wherein at least one of said bonding of the first and second subseries of pieces to be bonded comprises ultrasonic bonding.

8. The process of claim 1 wherein at least one of said bonding of the first and second subseries of pieces to be bonded comprises thermal bonding.

9. The process of claim 1 wherein said bonding of the first and second subseries of pieces to be bonded occurs at least in part substantially simultaneously.

10. The process of claim 1 wherein the pieces to be bonded comprise a disposable garment for absorbing human discharge.

11. The process of claim 10 wherein said bonding comprises forming a side seam in the disposable garment for absorbing human discharge.

12. The process of claim 11 wherein at least one of said bonding of the first and second subseries of pieces to be bonded comprises ultrasonic bonding.

13. The process of claim 11 wherein said bonding comprises forming a first side seam on a first side and a second side seam on a second side of the disposable garment for absorbing human discharge.

14. The process of claim 13 wherein said first and second side seams are formed substantially simultaneously.

15. The process of claim 14 wherein members of at least one of the first and second subseries of pieces to be bonded are folded prior to being bonded.

16. A continuous high speed process for ultrasonic bonding a series of pieces each to itself comprising:
supplying a series of pieces to be bonded,
splitting the series of pieces to be bonded alternatingly into first and second subseries of pieces to be bonded,
folding members of the first subseries of pieces to be bonded into bonding relative position,
folding members of the second subseries of pieces to be bonded into bonding relative position,
ultrasonically bonding the first subseries of pieces to be bonded to form a first series of bonded pieces, and
ultrasonically bonding the second subseries of pieces to be bonded to form a second series of bonded pieces.

17. The process of claim 16 additionally comprising,
combining the first and second series of bonded pieces to form a unified series of bonded product.

18. The process of claim 16 wherein the pieces to be bonded comprise disposable garment for absorbing human discharge.

19. The process of claim 18 wherein said bonding comprises forming a side seam in the disposable garment for absorbing human discharge.

20. The process of claim 18 wherein said ultrasonic bonding of the first and second subseries of pieces to be bonded comprises forming a first side seam on a first side and a second side seam on an opposed second side of the disposable garment for absorbing human discharge.

21. The process of claim 20 wherein the first and second side seams are formed substantially simultaneously.

22. A process for side seam bonding of a disposable pant-like garment for absorbing human discharge comprising
supplying a series of planar garment precursor pieces to be bonded,
splitting the series of pieces to be bonded alternatingly into first and second subseries of pieces to be bonded,
folding members of the first and second subseries of pieces to be bonded into bonding relative position,
sequentially ultrasonically bonding the folded members of the first subseries of pieces to be bonded to form a first series of bonded pieces, and
sequentially ultrasonically bonding the folded members of the second subseries of pieces to be bonded to form a second series of bonded pieces,
wherein a folded member of the first subseries of pieces to be bonded and a folded member of the second subseries of pieces to be bonded are bonded substantially simultaneously.

23. The process of claim 22 additionally comprising combining the first and second series of bonded pieces to form a unified series of bonded product.

24. The process of claim 22 wherein said bonding comprises forming a bond on opposite sides of the first and second subseries of pieces to be bonded, respectively.

* * * * *

UNITED STATES PATENT AND TRADEMARK OFFICE
CERTIFICATE OF CORRECTION

PATENT NO. : 6,183,576 B1  Page 1 of 1
DATED : February 6, 2001
INVENTOR(S) : Couillard et al.

It is certified that error appears in the above-identified patent and that said Letters Patent is hereby corrected as shown below:

Column 4,
Line 15, delete "cuffing" and substitute -- cutting --.

Column 7,
Line 44, delete "altematingly" and substitute -- alternatingly --.

Signed and Sealed this

Twenty-sixth Day of February, 2002

*Attest:*

JAMES E. ROGAN
*Attesting Officer*   *Director of the United States Patent and Trademark Office*